(12) United States Patent
Xing et al.

(10) Patent No.: US 12,037,303 B2
(45) Date of Patent: Jul. 16, 2024

(54) METHOD FOR PREPARING DIARYL P-PHENYLENEDIAMINE COMPOUNDS

(71) Applicant: Sennics Co., Ltd., Shanghai (CN)

(72) Inventors: Jinguo Xing, Shanghai (CN); Xiangyun Guo, Shanghai (CN); Zhimin Tang, Shanghai (CN)

(73) Assignee: Sennics Co., Ltd., Shanghai (CN)

( * ) Notice: Subject to any disclaimer, the term of this patent is extended or adjusted under 35 U.S.C. 154(b) by 0 days.

(21) Appl. No.: 18/148,370

(22) Filed: Dec. 29, 2022

(65) Prior Publication Data

US 2024/0076264 A1    Mar. 7, 2024

(30) Foreign Application Priority Data

Aug. 22, 2022 (CN) .......................... 202211007384.0

(51) Int. Cl.
| | | |
|---|---|---|
| *C07C 209/60* | (2006.01) | |
| *B01J 21/04* | (2006.01) | |
| *B01J 21/18* | (2006.01) | |
| *B01J 23/42* | (2006.01) | |
| *B01J 23/44* | (2006.01) | |

(52) U.S. Cl.
CPC ............. *C07C 209/60* (2013.01); *B01J 21/04* (2013.01); *B01J 21/18* (2013.01); *B01J 23/42* (2013.01); *B01J 23/44* (2013.01)

(58) Field of Classification Search
CPC ...... C07C 211/26; C07C 209/60; B01J 23/42; B01J 23/44
See application file for complete search history.

(56) References Cited

U.S. PATENT DOCUMENTS

| | | | | |
|---|---|---|---|---|
| 5,382,690 A | * | 1/1995 | Nagata .................. | C07C 209/28 564/396 |
| 10,793,510 B2 | * | 10/2020 | Guo ...................... | C07C 209/60 |
| 10,829,615 B2 | | 11/2020 | Gao et al. | |
| 11,008,281 B2 | | 5/2021 | Gao et al. | |
| 2018/0237376 A1 | | 8/2018 | Guo et al. | |
| 2021/0230099 A1 | | 7/2021 | Gao et al. | |

FOREIGN PATENT DOCUMENTS

| | | |
|---|---|---|
| CN | 101823978 A | 9/2010 |
| CN | 101844996 A | 9/2010 |
| CN | 102675129 A | 9/2012 |
| CN | 104629718 B | 1/2017 |
| CN | 110734380 A | 1/2020 |

OTHER PUBLICATIONS

U.S. Appl. No. 18/384,801, filed Oct. 27, 2023, Jinguo Xing et al.
U.S. Appl. No. 18/147,693, filed Dec. 28, 2022, Xiaoyin Zhou et al.
U.S. Appl. No. 18/148,408, filed Dec. 29, 2022, Jinguo Xing et al.
Xing, Jinguo et al., "Preparation and properties of diaryl-p-phenylenediamine antioxidants," Rubber Science and Technology, No. 9, pp. 25-29 (Sep. 30, 2017).

* cited by examiner

*Primary Examiner* — Alexander R Pagano
*Assistant Examiner* — Frank S. Hou
(74) *Attorney, Agent, or Firm* — Mei & Mark LLP; Manni Li

(57) ABSTRACT

A method for preparing a diaryl-p-phenylenediamine compound of Formula I comprises the steps of reacting a compound of Formula II and a compound of Formula III in a condensation dehydrogenation reaction in the presence of a solvent, a hydrogen acceptor, a water-carrying agent, and a catalyst; wherein $R_1$, $R_2$ and $R_3$ are independently selected and each is H, a C1-C8 alkyl, a C3-C8 cycloalkyl, a C1-C8 alkoxy, a C3-C8 cycloalkoxy, or phenyl; a and c are independently selected and each is an integer of 0 to 5, and b is an integer of 0 to 4:

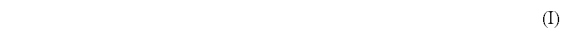

(I)

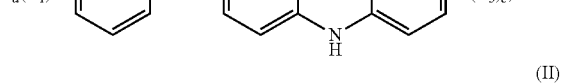

(II)

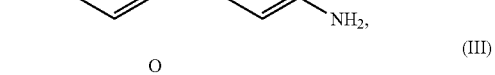

(III)

19 Claims, No Drawings

METHOD FOR PREPARING DIARYL P-PHENYLENEDIAMINE COMPOUNDS

CROSS-REFERENCE TO RELATED APPLICATIONS

The subject application claims priority on Chinese Patent Application No. 202211007384.0 filed on Aug. 22, 2022 in China. The contents and subject matters of the Chinese priority application are incorporated herein by reference.

TECHNICAL FIELD

The present invention relates to rubber chemicals, particularly, a method for preparing a diaryl p-phenylenediamine compound.

BACKGROUND ART

P-phenylenediamine compounds, including the derivatives thereof such as dialkyl-p-phenylenediamine, alkylaryl-p-phenylenediamine, and diaryl-phenylenediamine, are widely used antidegradants for rubber tires. Different types of p-phenylenediamine derivatives have different physicochemical properties and anti-aging properties. Among the three derivatives, diaryl-p-phenylenediamine has the best resistance to volatility, extraction, and migration. The representative antidegradant products of diaryl-p-phenylenediamine are antidegradant H (N,N'-diphenyl-p-phenylenediamine) and antidegradant 3100 (a mixture of N,N'-diphenyl-p-phenylenediamine, N,N'-ditolyl-p-phenylenediamine, and N-phenyl-N'-tolyl-p-phenylenediamine). Antidegradant 3100 is a typical after-effect p-phenylenediamine rubber antidegradant, which can effectively make up for the shortcomings of the current dominant p-phenylenediamine antidegradant 4020 (N-(1,3-dimethyl)butyl-N'-phenyl-p-phenylenediamine) and 4010NA (N-isopropyl-N'-phenyl-p-phenylenediamine) which have good anti-aging effect in the early stage but slightly poor in the later stage.

Chinese Patent CN104629718B discloses a process of synthesizing the antidegradant H by a reaction at 85° C. and using p-phenylenediamine and bromobenzene as the starting materials and a palladium complex of triphenylphosphine and binaphthyl diphenylphosphine as the catalysts. The reaction conditions are relatively mild; however, the organometallic complex catalysts are expensive, they are difficult to recover and reuse as supported catalysts, and the cost for recovery and reuse is very high.

Chinese Patent Application Publication CN106608827A discloses a preparation method of an aryl-substituted p-phenylenediamine, which uses N-phenyl-p-phenylenediamine, N-tolyl p-phenylenediamine, and cyclohexanone as the starting materials, phenol and o-cresol as the hydrogen acceptors, and supported precious metals as the catalysts to synthesize the antidegradant 3100 by a one-step reaction. However, the process needs to be performed at higher temperatures (220 to 280° C.).

Chinese Patent Application Publication CN110734380A discloses a preparation method of a diaryl-phenylenediamine or a mixture of the diaryl-phenyldiamines, which reacts p-nitroaniline and cyclohexanone or substituted cyclohexanone in a condensation dehydrogenation reaction in the presence of a solvent, a water-carrying agent, and a catalyst. In the process, p-nitroaniline is both a reactant and a hydrogen acceptor. However, the type of structures obtained in the products is limited, and the process is only suitable for the preparation of the diaryl p-phenylenediamine having a symmetrical structure or the mixture thereof, but not for the preparation of a single-component diaryl p-phenylenediamine with asymmetric structure. In addition, the cost of the p-nitroaniline as the starting material in the process is relatively high.

SUMMARY OF INVENTION

The present invention provides a method for preparing a diaryl-p-phenylenediamine compound, which solves the problems of high production cost, poor environmental protection, strong corrosiveness, and harsh reaction conditions in the current preparation process of diaryl p-phenylenediamine antidegradants.

The present invention provides a method for preparing a compound of Formula I:

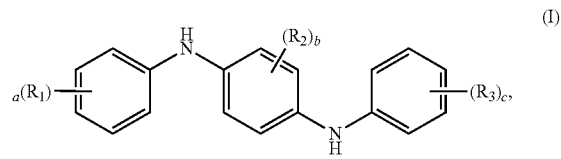

wherein $R_1$, $R_2$, $R_3$ are each independently selected and may be H, a C1-C8 alkyl, a C3-C8 cycloalkyl, a C1-C8 alkoxy, a C3-C8 cycloalkoxy, or phenyl; a and c each are independently selected integers of 0 to 5, b is an integer of 0 to 4, wherein the method of preparation comprises the steps of reacting a compound of Formula II and a compound of Formula III in a condensation dehydrogenation reaction in the presence of a solvent, a hydrogen acceptor, a water-carrying agent, and a catalyst to obtain the compound of Formula I:

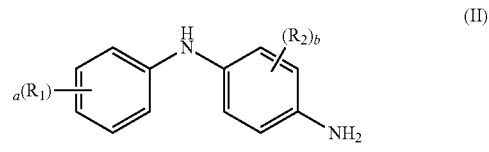

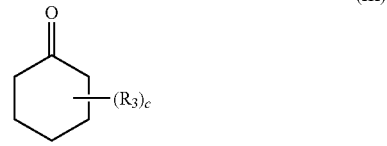

wherein in Formula II and Formula III, $R_1$, $R_2$ and $R_3$, a, b, and c are defined as above.

In the present invention, the hydrogen acceptor may be nitrobenzene, o-nitrotoluene, m-nitrotoluene, p-nitrotoluene, p-nitrophenol, o-nitrophenol, m-nitrophenol, p-nitroaniline, o-nitroaniline, m-nitroaniline, o-nitroanisole, m-nitroanisole, p-nitroanisole, o-nitrophenyl ethyl ether, m-nitrophenyl ethyl ether, p-nitrophenyl ethyl ether, styrene, α-methylstyrene, or a combination thereof.

In the present invention, the molar ratio of the compound of Formula II to the compound of Formula III is from 2:1 to 1:5, preferably from 3:2 to 1:4.

In the present invention, the molar ratio of the compound of Formula II to the hydrogen acceptor is from 3:2 to 1:5.

In the present invention, the catalyst may have the function of catalytic dehydrogenation and hydrogenation, and preferably, the catalyst is a precious metal supported catalyst.

In the present invention, the precious metal in the precious metal supported catalyst is Pd, Pt, Ru, or a combination thereof; the support is preferably C, Al$_2$O$_3$, diatomaceous earth, molecular sieve, or a combination thereof.

In the present invention, the precious metal supported catalyst may be Pd/C, Pt/C, Ru/C, Pd/Al$_2$O$_3$, Pt/diatomaceous earth, or Ru/molecular sieve.

In the present invention, the amount of the catalyst is 0.01 to 20 wt % of the mass of the compound of Formula II.

In the present invention, the solvent is a polar aprotic solvent; preferably, the solvent is dimethylformamide, dimethylacetamide, ethylene glycol dimethyl ether, diethylene glycol dimethyl ether, N-methylpyrrolidone, N-ethylpyrrolidone, or a combination thereof.

In the present invention, the water-carrying agent is a solvent that is insoluble in water but azeotropic with water. Preferably, the water-carrying agent is benzene, toluene, ethylbenzene, methylcyclohexane, ethylcyclohexane, chloroform, carbon tetrachloride, trichloroethane, tetrachloroethane, or a combination thereof.

In the present invention, the reaction is carried out at a temperature in the range of 100 to 180° C., preferably at a temperature range of 110 to 160° C.;

In the present invention, the reaction time is 2 to 20 hours;

In the present invention, the reaction is carried out under air or a protection gas, preferably in a nitrogen atmosphere.

DETAILED DESCRIPTION OF INVENTION

In the present invention, unless otherwise specified, percentage refers to mass percentage, and ratio refers to mass ratio.

In the present invention, when describing embodiments or examples, it should be understood that it is not intended to limit the present invention to these embodiments or examples. Conversely, all substitutes, modifications and equivalents of the methods and materials described in the present invention may be covered within the scope of the claims.

In the present invention, for the sake of conciseness, not all possible combinations of each technical feature in each embodiment or example are described. Thus, as long as there is no contradiction in the combination of these technical features, each technical feature in each embodiment or example may be arbitrarily combined, and all possible combinations should be considered to be within the scope of the specification.

In the present invention, an alkyl group is a monovalent saturated linear or branched hydrocarbon group containing 1-20, such as 1-8, carbon atoms. Examples of the alkyl group in the present invention include, but are not limited to, methyl, ethyl, propyl, 1-methylpropyl, isobutyl, and 1,3-dimethylbutyl.

In the present invention, a cycloalkyl group is a monovalent saturated hydrocarbon ring containing 3-20, such as 3-8, carbon atoms. Examples of the cycloalkyl group in the present invention include, but are not limited to, cyclopropyl, cyclobutyl, cyclopentyl, cyclohexyl, cycloheptyl, and cyclooctyl.

In the present invention, an alkoxy group is a combination of an alkyl group and an oxygen atom, which may contain 1-20, such as 1-8, carbon atoms. Examples of the alkoxy group in the present invention include, but are not limited to, methoxy, ethoxy, n-propoxy, and isopropoxy.

In the present invention, a cycloalkoxy group is to a combination of a cycloalkyl group and an oxygen atom, which may contain 3 to 20, such as 3 to 8, carbon atoms.

Examples of the alkoxy group in the present invention include, but are not limited to, cyclopropyloxy, cyclopentyloxy, and cyclohexyloxy.

The structural formula of the diaryl p-phenylenediamine compound of the present invention is represented by Formula I as follows:

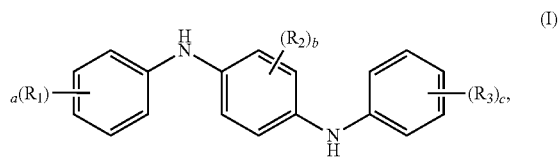

wherein R$_1$, R$_2$ and R$_3$ are each independently selected, and each may be H, a C1-C8 alkyl, a C3-C8 cycloalkyl, a C1-C8 alkoxy, a C3-C8 cycloalkoxy, or phenyl; a and c are independently selected, and each is an integer of 0 to 5, and b is an integer of 0 to 4.

In some embodiments, R$_1$, R$_2$ and R$_3$ are each independently H, a C10-C8 alkyl, or a C3-C8 cycloalkyl; or R$_1$, R$_2$ and R$_3$ are each independently H or a C1-C8 alkyl; or R$_1$, R$_2$ and R$_3$ are each independently H or methyl.

In some embodiments, R$_1$ and R$_3$ are each independently H, a C1-C8 alkyl, or a C3-C8 cycloalkyl, and R$_2$ is H.

In some embodiments, R$_1$ and R$_3$ are each independently H or a C1-C8 alkyl, and R$_2$ is H.

In some embodiments, R$_1$ and R$_3$ are each independently H or methyl, and R$_2$ is H.

In some embodiments, each R$_1$ is independently H, a C1-C8 alkyl, or a C3-C8 cycloalkyl, and R$_2$ and R$_3$ are both H.

In some embodiments, each R$_1$ is independently H or a C1-C8 alkyl, and R$_2$ and R$_3$ are both H.

In some embodiments, each R$_1$ is independently H or methyl, and R$_2$ and R$_3$ are both H.

In some embodiments, a and c are each independently an integer of 0 to 2.

In some embodiments, b is 0.

In some embodiments, a is an integer of 0 to 2, and c is 0.

In some embodiments, the compound of Formula I is N,N'-diphenyl-p-phenylenediamine, N-phenyl-N'-o-tolyl-p-phenylenediamine, or N-phenyl-N'-2,3-xylyl-p-phenylenediamine.

The preparation method of the present invention uses the compound of Formula II and the compound of Formula III as starting materials:

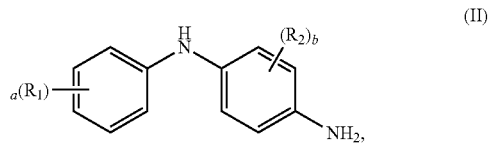

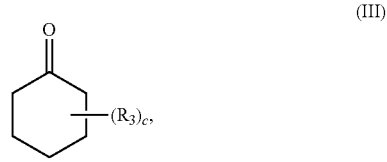

wherein R$_1$, R$_2$, R$_3$, a, b, c are as described above.

In the present invention, the starting materials, the compound of Formula II to the compound of III at a molar ratio of 2:1 to 1:5 may be used for the reaction. In some embodiments, the molar ratio of the compound of Formula II to the compound of III is 3:2 to 1:4, such as 1:1, 1:1.5, 1:2, or 1:3, which improves the yield and selectivity as well as product purity.

The reaction scheme of the present invention is as follows:

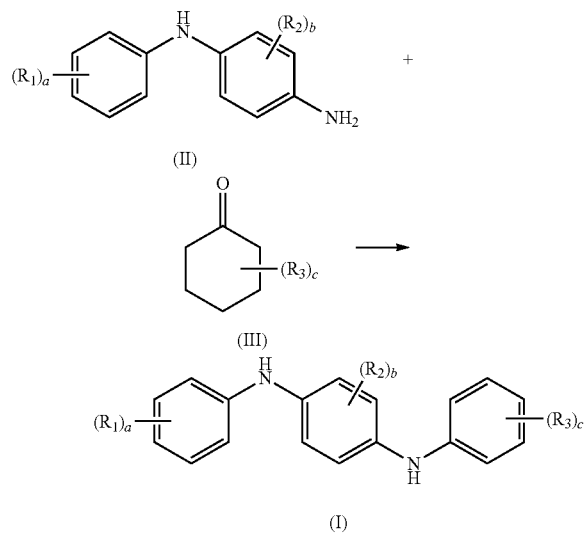

In particular, a monoaryl substituted p-phenylenediamine compound of Formula II and a cyclohexanone compound of Formula III undergo a condensation dehydrogenation reaction under the action of a hydrogen acceptor and a catalyst to form a diaryl substituted p-phenylenediamine substance, i.e., the compound of Formula I.

A catalyst suitable for the present invention may be a catalyst known in the art having catalytic dehydrogenation and hydrogenation functions. Preferably, the catalyst is a precious metal supported catalyst. The precious metal supported catalysts comprise precious metals as centers of catalytic activity and carriers for supporting the precious metals. In the precious metal supported catalyst suitable for the present invention, the precious metal is preferably Pd, Pt, or Ru, and the carrier is preferably one or more of C, $Al_2O_3$, diatomaceous earth, or molecular sieve. The precious metal supported catalysts are preferably one or more of Pd/C (i.e., Pd supported on carbon, same goes for other supported metal catalysts), Pt/C, Ru/C, Pd/$Al_2O_3$, Pt/diatomaceous earth, or Ru/molecular sieve. These catalysts have high catalytic activity, enabling milder reaction conditions. In the precious metal supported catalysts, the content (mass percentage) of the precious metals may be 1% to 10%, such as 2%, 3%, 5%, or 8%.

Those skilled in the art can adjust the specific amount of the catalyst according to the actual reaction. In a preferred embodiment, the amount of the catalyst is 0.01 to 20% by mass of the compound of Formula II, such as 0.02%, 0.03%, 0.05%, 0.08%, 0.1%, 0.2%, 0.5%, 0.8%, 1%, 2%, 5%, 8%, 10%.

In the present invention, the reaction is carried out in the presence of a solvent, a hydrogen acceptor, and a water-carrying agent.

The solvent suitable for the method of the present invention is preferably a polar aprotic solvent. For example, the solvent may be one or more of dimethylformamide, dimethylacetamide, ethylene glycol dimethyl ether, diethylene glycol dimethyl ether, N-methylpyrrolidone, or N-ethylpyrrolidone. The amount of the solvent may be adjusted by those skilled in the art according to the actual reaction.

In the present invention, the hydrogen acceptor is a compound that is easily reduced, that is, a compound that can accept hydrogen from the condensation of the compound of Formula II and the compound of Formula III under the action of a catalyst. In the present invention, the compound of Formula II react with the compound of Formula III in a condensation dehydrogenation reaction, and the hydrogen acceptor undergoes a hydrogenation-reduction reaction. The hydrogen acceptor suitable for the present invention is preferably one or more of nitrobenzene, o-nitrotoluene, m-methylnitrotoluene, p-nitrotoluene, p-nitrophenol, o-nitrophenol, m-nitrophenol, p-nitroaniline, o-nitroaniline, m-nitroaniline, o-nitroanisole, m-nitroanisole, p-nitroanisole, o-nitrophenyl ethyl ether, m-nitrophenyl ethyl ether, p-nitrophenyl ethyl ether, styrene, or α-methylstyrene. The use of these hydrogen acceptors reduces the temperature required for the reaction. In the present invention, the compound of Formula II and the hydrogen acceptor may be reacted in a molar ratio of from 3:2 to 1:5, such as 1:1, 1:1.5, 1:2, 1:3, 1:4, so as to improve the reaction efficiency and product purity.

In the present invention, the water-carrying agent is used to separate water generated by the reaction from the reaction system. It is usually a solvent insoluble in water but azeotropic with water. In some embodiments, the water-carrying agent suitable for the present invention is one or more of benzene, toluene, ethylbenzene, methylcyclohexane, ethylcyclohexane, chloroform, carbon tetrachloride, trichloroethane, or tetrachloroethane. The amount of the water carrying agent can be adjusted by those skilled in the art according to the actual reaction.

In the present invention, the reaction of the compound of Formula II and the compound of Formula III is a condensation dehydrogenation reaction. The reaction may be carried out at 100 to 180° C., preferably at 110 to 160° C., such as 120° C., 125° C., 130° C., 140° C., and 150° C. Those skilled in the art can determine the reaction time according to the actual reaction. Usually, the reaction time is 2 to 20 hours, such as 3 hours, 4 hours, 5 hours, 6 hours, 8 hours, or 10 hours.

In the present invention, the reaction may be carried out in air or in a protection gas, such as in a nitrogen atmosphere. The use of a protection gas reduces the risk of explosion and prevents the toluene-based water-carrying agent in the vapor phase space from forming explosive mixtures with air.

In some embodiments, the method of the present invention comprises: refluxing a reaction mixture comprising a compound of Formula II, a compound of Formula III, a catalyst, a solvent, a hydrogen acceptor, and a water-carrying agent at 100 to 180° C., preferably 110 to 160° C., during which the generated water is continuously removed until no more water is separated, and removing the catalyst, the solvent, by-product (e.g., a reduction product of the hydrogen acceptor), the water-carrying agent, and excess starting materials, if any, to obtain a compound of Formula I. Solid catalysts may be removed by filtration. Conventional vacuum distillation may be used to remove the solvent, by-products, the water-carrying agents, and unreacted starting materials.

The method of the present invention is suitable for preparing symmetrical or asymmetric diaryl-substituted p-phenylenediamine compounds. For example, the compound with the benzene ring where $R_1$ is located and the benzene ring where $R_3$ is located may be the same or different.

In some embodiments, the method of the present invention may be used to prepare the antidegradant H. The method comprises a step of reacting N-phenyl-p-phenylenediamine with cyclohexanone in the presence of a solvent, a hydrogen acceptor, a water-carrying agent, and a catalyst. In these embodiments, the molar ratio of N-phenyl-p-phenylenediamine to cyclohexanone may be from 2:1 to 1:4, e.g., 3:2 to 1:3.

In some embodiments, the method of the present invention may be used to prepare the antidegradant N-phenyl-N'-tolyl-p-phenylenediamine, such as N-phenyl-N'-o-tolyl-p-phenylenediamine. The method comprises a step of reacting N-tolyl-p-phenylenediamine with cyclohexanone in the presence of a solvent, a hydrogen acceptor, a water-carrying agent, and a catalyst. In these embodiments, the molar ratio of N-tolyl-p-phenylenediamine to cyclohexanone may be from 2:1 to 1:5, e.g., 3:2 to 1:4.

In some embodiments, the method of the present invention may be used to prepare the antidegradant N-phenyl-N'-xylyl-p-phenylenediamine, such as N-phenyl-N'-2,3-xylyl-p-phenylenediamine. The method comprises a step of reacting N-xylyl-p-phenylenediamine with cyclohexanone in the presence of a solvent, a hydrogen acceptor, a water-carrying agent and a catalyst. In these embodiments, the molar ratio of N-xylyl-p-phenylenediamine to cyclohexanone may be from 2:1 to 1:4, e.g., 3:2 to 1:3.

In the preparation method of the present invention, the starting materials are readily available. Due to the unique reaction route in the reaction, the post-treatment process of the reaction is relatively simple and there is no need to use a large amount of water. At the same time, the reaction conditions are mild and do not corrode the reaction equipment. The reaction temperature is low and there is no need to react at a relatively high temperature. The preparation method saves cost as the price of the starting materials is lower than p-nitroaniline. Therefore, the preparation method of the present invention is environmentally friendly, less polluting, and can provide better economic benefits.

The present invention is further described in the following specific examples. It should be understood that these examples are merely illustrative and are not intended to limit the scope of the present invention. The methods, reagents, and materials used in the examples, unless otherwise stated, are conventional methods, reagents, and materials in the art. The starting materials used in the examples are commercially available.

EXAMPLE 1

92 g (0.5 mol) N-phenyl-p-phenylenediamine, 49 g (0.5 mol) cyclohexanone, 43.1 g (0.35 mol) nitrobenzene, 0.02 g catalyst Pd/C (Pd content 5%, water content 60%), 100 mL dimethylformamide, and 20 mL benzene are added to a four-mouth flask equipped with a water separator, a condenser, and a thermometer. The reaction system is heated to raise the temperature to 110° C. for reflux and reaction, and the water separated from the condensate is continuously removed. After the reaction temperature is held for 20 hrs, no more water is separated from the condensate. The temperature is cooled down, and the catalyst is filtered. The filtrate is distilled under reduced pressure to distill benzene, dimethylformamide, a small amount of excessive starting materials, and by-products to obtain 54.2 g residual liquid. The content of the antidegradant H (N,N'-diphenyl-p-phenylenediamine) is measured by GC area normalization method to be 96%:

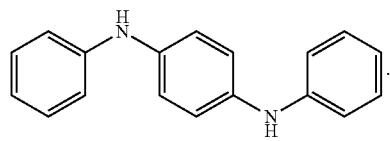 [SMILES: c1ccc(Nc2ccc(Nc3ccccc3)cc2)cc1]

EXAMPLE 2

99 g (0.5 mol) N-o-tolyl-p-phenylenediamine, 98 g (1 mol) cyclohexanone, 123 g (1 mol) nitrobenzene, 0.2 g catalyst Pd/C (Pd content 5%, water content 60%), 120 mL dimethylacetamide, and 20 mL toluene are added to a four-mouth flask equipped with a water separator, a condenser, and a thermometer. The reaction system is heated to raise the temperature to 110° C. for reflux and reaction, and the water separated from the condensate is continuously removed. After the reaction temperature is held for 6 hrs, no more water is separated from the condensate. The temperature is cooled down, and the catalyst is filtered. The filtrate is distilled under reduced pressure to distill toluene, dimethylacetamide, a small amount of excessive starting materials, and by-products to obtain 141.2 g residual liquid. The content of N-phenyl-N'-o-tolyl-p-phenylenediamine is measured by GC area normalization method to be 97%:

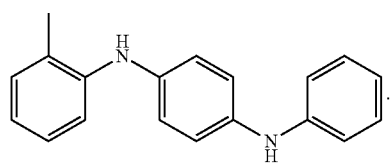 [SMILES: Cc1ccccc1Nc1ccc(Nc2ccccc2)cc1]

EXAMPLE 3

99 g (0.5 mol) N-o-tolyl-p-phenylenediamine, 196 g (2 mol) cyclohexanone, 104 g (1 mol) styrene, 1 g catalyst Pd/C (Pd content 5%, water content 60%), 200 mL N-methylpyrrolidone, and 20 mL toluene are added to a four-mouth flask equipped with a water separator, a condenser, and a thermometer. The reaction system is heated to raise the temperature to 110° C. for reflux and reaction, and the water separated from the condensate is continuously removed. After the reaction temperature is held for 5 hrs, no more water is separated from the condensate. The temperature is cooled down, and the catalyst is filtered. The filtrate is distilled under reduced pressure to distill toluene, ethyl benzene as a by-product, and N-methylpyrrolidone as a solvent to obtain 136.5 g residual liquid. The content of N-phenyl-N'-o-tolyl-p-phenylenediamine is measured by GC area normalization method to be 93.5%:

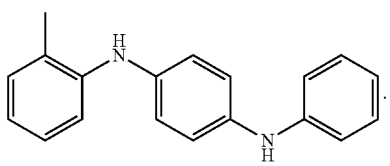 [SMILES: Cc1ccccc1Nc1ccc(Nc2ccccc2)cc1]

EXAMPLE 4

106 g (0.5 mol) N-2,3-xylyl-p-phenylenediamine, 49 g (0.5 mol) cyclohexanone, 43.1 g (0.35 mol) nitrobenzene, 8 g catalyst Pd/C (Pd content 5%, water content 60%), 100 mL dimethylformamide, and 20 mL toluene are added to a four-mouth flask equipped with a water separator, a condenser, and a thermometer. The reaction system is heated to raise the temperature to 110° C. for reflux and reaction, and the water separated from the condensate is continuously removed. After the reaction temperature is held for 5 hrs, no more water is separated from the condensate. The temperature is cooled down, and the catalyst is filtered. The filtrate is distilled under reduced pressure to distill toluene, dimethylformamide, a small amount of excessive starting materials, and by-products to obtain 135.6 g residual liquid. The content of N-phenyl-N'-2,3-xylyl-p-phenylenediamine is measured by GC area normalization method to be 95.6%:

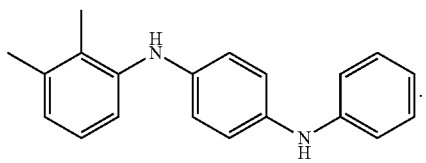 [SMILES: Cc1cccc(Nc2ccc(Nc3ccccc3)cc2)c1C]

EXAMPLE 5

106 g (0.5 mol) N-2,3-xylyl-p-phenylenediamine, 88.2 g (0.9 mol) cyclohexanone, 73.8 g (0.6 mol) nitrobenzene, 17 g catalyst Pd/C (Pd content 5%, water content 60%), 120 mL dimethylformamide, and 20 mL toluene are added to a four-mouth flask equipped with a water separator, a condenser, and a thermometer. The reaction system is heated to raise the temperature to 120° C. for reflux and reaction, and the water separated from the condensate is continuously removed. After the reaction temperature is held for 3 hrs, no more water is separated from the condensate. The temperature is cooled down, and the catalyst is filtered. The filtrate is distilled under reduced pressure to distill toluene, dimethylformamide, a small amount of excessive starting materials, and by-products to obtain 150 g residual liquid. The content of N-phenyl-N'-2,3-xylyl-p-phenylenediamine is measured by GC area normalization method to be 96%:

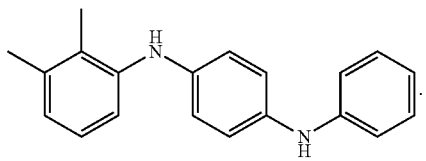 [SMILES: Cc1cccc(Nc2ccc(Nc3ccccc3)cc2)c1C]

EXAMPLE 6

106 g (0.5 mol) N-2,3-xylyl-p-phenylenediamine, 53.9 g (0.55 mol) cyclohexanone, 114.4 g (1.1 mol) styrene, 16 g catalyst Pt/C (Pt content 5%, water content 60%), 120 mL diethylene glycol dimethyl ether, and 20 mL toluene are added to a four-mouth flask equipped with a water separator, a condenser, and a thermometer. The reaction system is heated to raise the temperature to 125° C. for reflux and reaction, and the water separated from the condensate is continuously removed. After the reaction temperature is held for 4 hrs, no more water is separated from the condensate. The temperature is cooled down, and the catalyst is filtered. The filtrate is distilled under reduced pressure to distill toluene, diethylene glycol dimethyl ether, ethylbenzene as a by-product, and a small amount of excessive starting materials to obtain 151.3 g residual liquid. The content of N-phenyl-N'-2,3-xylyl-p-phenylenediamine is measured by GC area normalization method to be 95%:

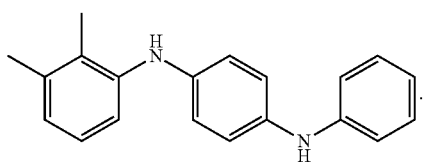 [SMILES: Cc1cccc(Nc2ccc(Nc3ccccc3)cc2)c1C]

EXAMPLE 7

106 g (0.5 mol) N-2,3-xylyl-p-phenylenediamine, 98 g (1 mol) cyclohexanone, 86.1 g (0.7 mol) nitrobenzene, 10 g catalyst Pt/Al$_2$O$_3$ (Pd content 3%, water content 60%), 120 mL dimethylformamide, and 20 mL toluene are added to a four-mouth flask equipped with a water separator, a condenser, and a thermometer. The reaction system is heated to raise the temperature to 130° C. for reflux and reaction, and the water separated from the condensate is continuously removed. After the reaction temperature is held for 6 hrs, no more water is separated from the condensate. The temperature is cooled down, and the catalyst is filtered. The filtrate is distilled under reduced pressure to distill toluene, dimethylformamide, and a small amount of excessive starting materials to obtain 148.5 g residual liquid. The content of N-phenyl-N'-2,3-xylyl-p-phenylenediamine is measured by GC area normalization method to be 97%:

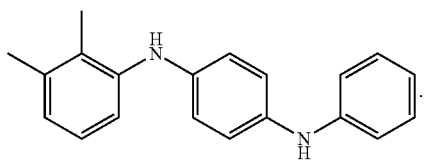 [SMILES: Cc1cccc(Nc2ccc(Nc3ccccc3)cc2)c1C]

We claim:
1. A method for preparing a compound of Formula I:

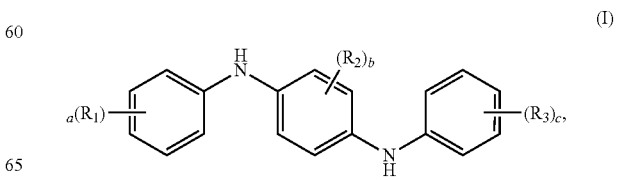

comprising:
reacting a compound of Formula II and a compound of Formula III in a condensation dehydrogenation reaction in presence of a solvent, a hydrogen acceptor, a water-carrying agent, and a catalyst to obtain the compound of Formula I:

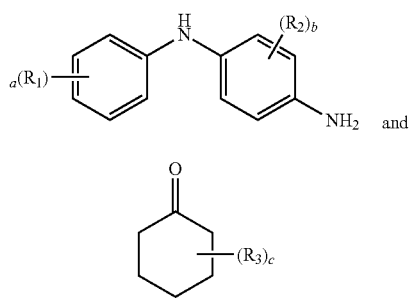

wherein $R_1$, $R_2$ and $R_3$ are independently selected, and each is H, a C1-C8 alkyl, a C3-C8 cycloalkyl, a C1-C8 alkoxy, a C3-C8 cycloalkoxy, or phenyl; a and c are independently selected, and each is an integer of 0 to 5, and b is an integer of 0 to 4, and the hydrogen acceptor is nitrobenzene, o-nitrotoluene, m-nitrotoluene, p-nitrotoluene, p-nitrophenol, o-nitrophenol, m-nitrophenol, o-nitroanisole, m-nitroanisole, p-nitroanisole, o-nitrophenyl ethyl ether, m-nitrophenyl ethyl ether, m-nitrophenyl ethyl ether, p-nitrophenyl ethyl ether, styrene, α-methylstyrene, or a combination thereof.

2. The method according to claim 1, wherein a molar ratio of the compound of Formula II to the compound of Formula III is from 2:1 to 1:5.

3. The method according to claim 1, wherein a molar ratio of the compound of Formula II to the compound of Formula III is from 3:2 to 1:4.

4. The method according to claim 1, wherein the molar ratio of the compound of Formula II to the hydrogen acceptor is from 3:2 to 1:5.

5. The method according to claim 1, wherein the catalyst has functions of catalytic dehydrogenation and hydrogenation.

6. The method according to claim 1, wherein the catalyst is a precious metal supported catalyst.

7. The method according to claim 6, wherein the precious metal in the precious metal supported catalyst is Pd, Pt, Ru, or a combination thereof;
the support is C, $Al_2O_3$, diatomaceous earth, molecular sieve, or a combination thereof.

8. The method according to claim 6, wherein the precious metal supported catalyst is Pd/C, Pt/C, Ru/C, Pd/$Al_2O_3$, Pt/diatomaceous earth, Ru/molecular sieve, or a combination thereof.

9. The method according to claim 1, wherein n amount of the catalyst is 0.01 to 20 wt % of the mass of the compound of Formula II.

10. The method according to claim 1, wherein the solvent is a polar aprotic solvent.

11. The method according to claim 1, wherein the solvent is dimethylformamide, dimethylacetamide, ethylene glycol dimethyl ether, diethylene glycol dimethyl ether, N-methylpyrrolidone, N-ethylpyrrolidone, or a combination thereof.

12. The method according to claim 1, wherein the water-carrying agent is a solvent that is insoluble in water but azeotropic with water.

13. The method according to claim 1, wherein the water-carrying agent is benzene, toluene, ethylbenzene, methylcyclohexane, ethylcyclohexane, chloroform, carbon tetrachloride, trichloroethane, tetrachloroethane, or a combination thereof.

14. The method according to claim 1, wherein c is an integer of 1 to 5.

15. The method according to claim 14, wherein $R_3$ is a C3-C8 cycloalkyl, a C1-C8 alkoxy, a C3-C8 cycloalkoxy, or phenyl.

16. The method according to claim 1, wherein a is an integer of 1 to 5.

17. The method according to claim 16, wherein $R_1$ is a C3-C8 cycloalkyl, a C1-C8 alkoxy, a C3-C8 cycloalkoxy, or phenyl.

18. The method according to claim 1, wherein b is 0, and $R_1$ is a C3-C8 cycloalkyl, a C1-C8 alkoxy, a C3-C8 cycloalkoxy, or phenyl.

19. The method according to claim 1, wherein b is an integer of 1 to 4.

* * * * *